(12) United States Patent
Yeshurun et al.

(10) Patent No.: US 7,998,119 B2
(45) Date of Patent: Aug. 16, 2011

(54) SYSTEM AND METHOD FOR DELIVERING FLUID INTO FLEXIBLE BIOLOGICAL BARRIER

(75) Inventors: Yehoshua Yeshurun, Haifa (IL); Meir Hefetz, Mizpeh Harashim (IL); Yoel Sefi, Kibutz Malkia (IL); Yotam Levin, Savion (IL); Gilad Lavi, Rishon Letzion (IL)

(73) Assignee: Nano Pass Technologies Ltd., Rehovot (IL)

( * ) Notice: Subject to any disclaimer, the term of this patent is extended or adjusted under 35 U.S.C. 154(b) by 1789 days.

(21) Appl. No.: 11/134,411

(22) Filed: May 23, 2005

(65) Prior Publication Data

US 2005/0209566 A1 Sep. 22, 2005

Related U.S. Application Data

(63) Continuation-in-part of application No. PCT/IL2004/001065, filed on Nov. 18, 2004.

(60) Provisional application No. 60/520,667, filed on Nov. 18, 2003, provisional application No. 60/581,711, filed on Jun. 23, 2004, provisional application No. 60/651,861, filed on Feb. 11, 2005.

(51) Int. Cl.
*A61M 5/00* (2006.01)

(52) U.S. Cl. ........................................................ 604/173

(58) Field of Classification Search .................. 604/116, 604/117, 20, 272–274; 606/131, 201, 204, 606/204.35

See application file for complete search history.

(56) References Cited

U.S. PATENT DOCUMENTS

| | | | |
|---|---|---|---|
| 2,402,306 A | 6/1946 | Turkel | |
| 2,457,464 A | 12/1948 | Grose | |
| 3,841,307 A | 10/1974 | Friedell | |
| 3,920,001 A | 11/1975 | Edwards | |
| 3,964,482 A * | 6/1976 | Gerstel et al. | 604/890.1 |
| 4,299,219 A | 11/1981 | Norris, Jr. | |
| 5,100,387 A * | 3/1992 | Ng | 604/116 |
| 5,199,952 A | 4/1993 | Marshall, Sr. et al. | |
| 5,478,315 A | 12/1995 | Brothers et al. | |
| 6,423,051 B1 * | 7/2002 | Kaplan et al. | 604/506 |
| 6,440,096 B1 * | 8/2002 | Lastovich et al. | 604/27 |
| 6,464,865 B2 | 10/2002 | Tipton et al. | |
| 6,533,949 B1 | 3/2003 | Yeshurun | |

(Continued)

FOREIGN PATENT DOCUMENTS

WO WO03/074102 3/2003

*Primary Examiner* — Manuel A Mendez
(74) *Attorney, Agent, or Firm* — Mark Friedman (57) ABSTRACT

A system and method for delivering fluid into a flexible biological barrier employs a microneedle structure wherein a final position of microneedles inserted into the biological barrier is generally sideways projecting from the delivery configuration instead of the conventional downwards projecting arrangement. The microneedles project from a relief surface which is distinct from a primary biological-barrier contact region of the delivery configuration, and is typically angled upwards away from the biological barrier. During insertion, the contact region is brought into contact with the biological barrier and moved parallel to the surface of the flexible biological barrier so as to generate a boundary between a stretched portion and a non-stretched portion of the barrier. Typically concurrently with this motion, the microneedles penetrate into the flexible biological barrier such that, at the end of the motion, the microneedles extend into the flexible biological barrier from the boundary region in a direction towards the non-stretched portion. Fluid is then injected through the bores of the hollow microneedles towards non-stretched portion.

11 Claims, 8 Drawing Sheets

U.S. PATENT DOCUMENTS

| | | |
|---|---|---|
| 6,569,123 B2 | 5/2003 | Alchas |
| 6,569,143 B2 | 5/2003 | Alchas |
| 6,689,118 B2 | 2/2004 | Alchas |
| 6,776,776 B2 | 8/2004 | Alchas |
| 6,843,781 B2 | 1/2005 | Alchas |
| 6,971,999 B2 | 12/2005 | Py et al. |
| 7,052,483 B2 | 5/2006 | Wojcik |
| 7,108,681 B2 * | 9/2006 | Gartstein et al. ............ 604/173 |
| 7,258,805 B2 | 8/2007 | Stemme et al. |
| 2003/0050602 A1 | 3/2003 | Pettis et al. |
| 2003/0171716 A1 | 9/2003 | Ejlersen |
| 2005/0010193 A1 | 1/2005 | Laurent et al. |
| 2006/0206164 A1 | 9/2006 | Gavronsky |

* cited by examiner

SYSTEM AND METHOD FOR DELIVERING FLUID INTO FLEXIBLE BIOLOGICAL BARRIER

This application is a continuation in part of International Application No. PCT/IL04/001065 filed Nov. 18, 2004, which itself benefits from the priority of U.S. Provisional Patent Application No. 60/520,667 filed Nov. 18, 2003, and U.S. Provisional Patent Application No. 60/581,711 filed Jun. 23, 2004. This application also benefits from the priority of U.S. Provisional Patent Application No. 60/651,861 filed Feb. 11, 2005.

FIELD AND BACKGROUND OF THE INVENTION

The present invention relates to systems and methods for delivering fluids through a flexible biological barrier and, in particular, systems and methods employing microneedles for such purpose.

Intradermal drug delivery is known to be advantageous for a range of different medications and treatments, such as immunization, immunomodulation, gene delivery, dermatology, allergy, hypersensitivity and cosmetics. Conventionally, intradermal drug delivery is performed by a skilled medical professional using a hypodermic needle positioned bevel-up at a shallow angle relative to the skin surface. Care is required to achieve the correct depth of penetration to ensure successful injection within the dermal layers rather than subcutaneously. The bevel-up needle orientation is needed in order to facilitate positive engagement of the needle with the skin surface at such shallow angles and is anyway the standard practice with any acute angle hypodermic needle insertion (including for example for venipuncture into deeper layers). The use of hypodermic needles for intradermal delivery is known to be painful, since nerve endings in the dermal layer are typically severed by the relatively large needles used.

Further, it has been hypothesized that intraepidermal delivery of drugs, such as vaccines, may have a further enhanced biological effect. Despite its promising prospects, this approach has been largely neglected to date since no delivery devices were available for such shallow application.

Much interest has been shown in development of drug delivery devices which do not require skilled operation, for example, for self-administration of drugs by patients. One approach is that of a "mini-needle" device with an actuator which selectively deploys or retracts the needle so as to penetrate to a limited depth within the dermal layers. Examples of such a device are commercially available from Becton, Dickinson & Co. (USA) and are described in U.S. Pat. Nos. 6,843,781, 6,776,776, 6,689,118, 6,569,143, 6,569,123 and 6,494,865. The needle cannula of such devices typically projects between 1 and 2 millimeters, thereby defining the depth of penetration of the delivery system. Since the already-reduced-length bevel of the needle tip itself has a length of at least 0.8 mm, devices based on conventional needle structures of this type (i.e., a hollow metal cylinder with a beveled point) cannot readily be used for sealed fluid delivery to penetration depths less than 1 mm.

As an alternative to conventional needle structures, many attempts have been made to develop "microneedle" structures using various micromachining technologies and various materials. An early example of the "microneedle" approach may be found in U.S. Pat. No. 3,964,482 to Gerstel et al., issued in 1976, which discloses a drug delivery device for percutaneously administering a drug by use of microneedles (projections) of dimensions up to 10 microns to puncture the stratum corneum, thereby allowing the drug to reach the epidermis. The device has multiple needles projecting outwardly from one surface and, in one implementation, delivers a drug from a reservoir via central bores of the microneedles.

In the three decades since Gerstel et al., many microneedle devices have been proposed, but none has yet achieved commercial success as a widespread clinical product due to a number of practical problems. A first major problem of many microneedle designs relates to mechanical weakness of the microneedles which tend to fracture on contact with the skin, particularly when exposed to shear forces due to lateral movement. A second problem relates to blockage of the bores of hollow microneedles due to punching-out of a plug of tissue during insertion through the skin. Additionally, many needle designs have relatively thin walls causing fragility, and a blunt interface, requiring excessive penetration forces to overcome skin elasticity. These problems are effectively addressed by a microneedle structure disclosed in co-assigned U.S. Pat. No. 6,533,949, which is hereby incorporated by reference in its entirety. The aforementioned microneedle structures also help to overcome a further problem of microneedle devices, namely, that of ensuring effective penetration of the highly elastic skin barrier. Various structures and techniques for employing the aforementioned microneedle structure to achieve enhanced penetration are disclosed in co-assigned PCT Patent Application Publication No. WO 03/074102 A2, which is also hereby incorporated by reference in its entirety.

A still further problem which hampers use of microneedles, particularly for intradermal delivery of fluids, is the risk of leakage of fluid around the microneedles. Specifically, injection of fluids through the hollow microneedles typically generates a back-pressure which tends to expel the microneedles from their incisions. Attempts to prevent expulsion of the microneedles by application of downward force (i.e., towards the skin) on the microneedle device compresses the underlying tissue. This compression increases the fluid impedance opposing injection of the fluid, thereby also interfering with delivery of the fluid to the target tissue. Further, in many designs the fluid flow channels extend all the way to the tip, causing a structural dependence between those two elements. This limits the ability to increase flow channel size to allow greater flow without blunting the microneedle and greatly increasing the force required to achieve penetration, and the reaction forces exerted on the structures by the skin.

There is therefore a need for a system and method for delivering a fluid into a flexible biological barrier which would provide a reliable seal between the microneedles and the biological barrier, and which would reduce the aforementioned back-pressure expulsion effect on the microneedles and prevent leakage.

SUMMARY OF THE INVENTION

The present invention is a microneedle system and method for delivering a fluid into a flexible biological barrier.

According to the teachings of the present invention there is provided, a method for delivering a fluid into a flexible biological barrier, the method comprising: (a) moving at least one contact surface in contact with the flexible biological barrier in a motion having a component parallel to the surface of the flexible biological barrier so as to generate a boundary region between a stretched portion of the flexible biological barrier and a non-stretched portion of the flexible biological barrier; (b) causing at least one hollow microneedle to penetrate into the flexible biological barrier such that, at the end of the moving, the at least one hollow microneedle extends into the flexible biological barrier from the boundary region in a direction towards the non-stretched portion; and (c) delivering a fluid through the at least one hollow microneedle towards the non-stretched portion.

According to a further feature of the present invention, the moving and the causing are performed concurrently.

According to a further feature of the present invention, the at least one hollow microneedle is mechanically associated with the contact surface such that the at least one hollow microneedle penetrates into the flexible biological barrier as a result of the moving.

According to a further feature of the present invention, the contact surface is an edge of a block of material, and wherein the at least one hollow microneedle is deployed on a face of the block, the edge bordering the face.

According to a further feature of the present invention, the edge is formed between two substantially orthogonal faces provided by the block.

According to a further feature of the present invention, the edge is substantially perpendicular to the component of the motion parallel to the surface.

According to a further feature of the present invention, the face is ahead of the edge during the moving.

According to a further feature of the present invention, the at least one hollow microneedle is implemented as a linear array of a plurality of hollow microneedles deployed on the face, the linear array extending substantially parallel to the edge.

According to a further feature of the present invention, the at least one hollow microneedle has a height and terminates at a penetrating tip, a distance from the edge to a perpendicular projection of the penetrating tip onto the face being no greater than the height.

According to a further feature of the present invention, at least part of the at least one contact surface is provided by a surface of the at least one hollow microneedle.

According to a further feature of the present invention, the at least one hollow microneedle has a bore for delivery of fluid into the biological barrier, the at least one hollow microneedle extending into the flexible biological barrier with the bore extending at an angle of no greater than 45 degrees to an initial plane of the surface of the flexible biological barrier.

There is also provided according to the teachings of the present invention, a method for delivering a fluid into a flexible biological barrier, the method comprising: (a) providing a delivery device including a contact region and a relief region, the relief region having at least one hollow microneedle deployed thereon; (b) bringing the device against the biological barrier so that the contact region touches the biological barrier and the relief region does not contact the biological barrier; and (c) moving the device with a component of the motion parallel to the surface of the biological barrier so as to mechanically deform the biological barrier to bring the biological barrier into contact with at least part of the relief region such that the at least one microneedle penetrates into the biological barrier.

According to a further feature of the present invention, the contact region includes a substantially planar contact surface, and wherein the relief region includes a substantially planar relief surface, the contact surface and the relief surface forming between them an angle of no more than about 150 degrees.

According to a further feature of the present invention, the contact surface and the relief surface form between them an angle of no more than about 130 degrees.

According to a further feature of the present invention, the contact surface and the relief surface are substantially orthogonal.

According to a further feature of the present invention, the contact surface and the relief surface meet at an edge region.

According to a further feature of the present invention, the at least one hollow microneedle has a bore for delivery of fluid into the biological barrier, the bore extending at an angle of no greater than 45 degrees to the contact surface.

According to a further feature of the present invention, the at least one hollow microneedle has a height and terminates at a penetrating tip, a distance of the penetrating tip from the plane of the contact surface being no greater than the height.

According to a further feature of the present invention, the at least one hollow microneedle has a fluid flow bore intersecting with a downward-facing bevel surface of the microneedle to define a downward-facing fluid release aperture.

According to a further feature of the present invention, the at least one hollow microneedle includes: (a) at least one wall standing substantially perpendicular to the relief region surface, the at least one wall being deployed so as to define an open shape as viewed from above the relief region surface, the open shape having an included area; and (b) an inclined surface inclined so as to intersect with the at least one wall, the intersection of the inclined surface with the at least one wall defining at least one cutting edge, wherein the open shape is oriented to be open towards the contact region.

According to a further feature of the present invention, the at least one hollow microneedle has a height less than one millimeter.

According to a further feature of the present invention, the at least one hollow microneedle is implemented as a linear array of a plurality of microneedles.

According to a further feature of the present invention, the moving the device so as to mechanically deform the biological barrier is performed so as to raise a portion of the biological barrier above an initial plane of the biological barrier such that the at least one microneedle penetrates into the raised portion of the biological barrier.

According to a further feature of the present invention, the fluid is delivered through the at least one hollow microneedle into the raised portion of the biological barrier.

There is also provided according to the teachings of the present invention, a method for delivering a fluid into a flexible biological barrier, the method comprising: (a) providing a delivery device including at least one hollow microneedle projecting no more than one millimeter from a surface of the device, the at least one hollow microneedle having a fluid delivery bore defining a flow vector; and (b) mechanically deforming the flexible biological barrier and causing the at least one hollow microneedle to penetrate the flexible biological barrier in such a manner that the flow vector forms an angle of between 45 degrees and minus 15 degrees with an initial plane of the flexible barrier.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a microneedle system and method for delivering a fluid into a flexible biological barrier.

The principles and operation of systems and methods according to the present invention may be better understood with reference to the drawings and the accompanying description.

Figure 1:
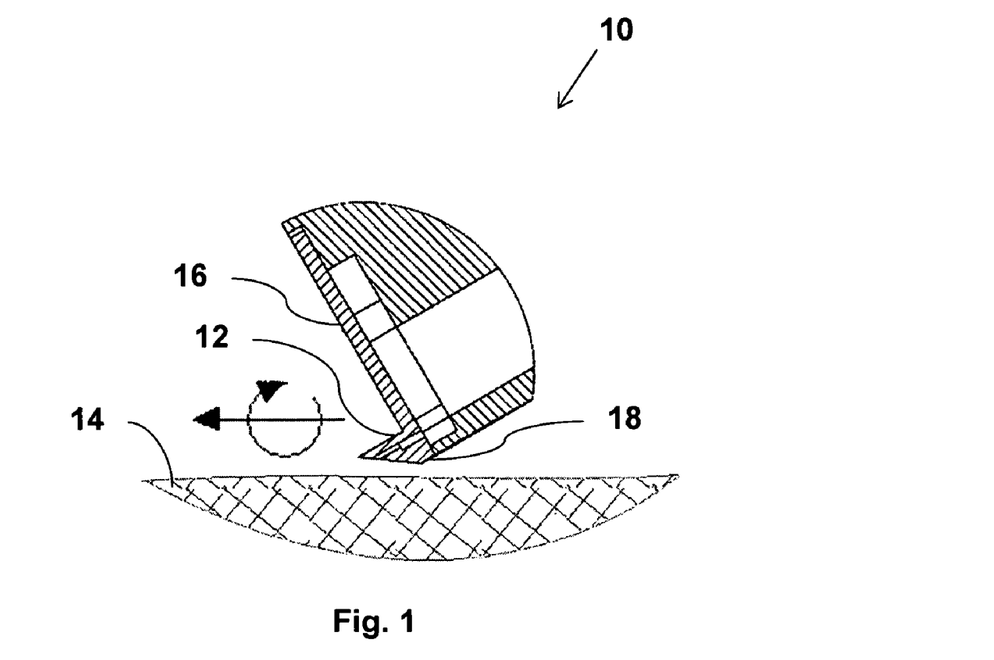
FIGS. 1 and 2 are schematic side cross-sectional views of a microneedle fluid delivery device, constructed and operative according to the teachings of the present invention, prior to and subsequent to insertion into a flexible biological barrier according to the method of the present invention.
Figure 2:
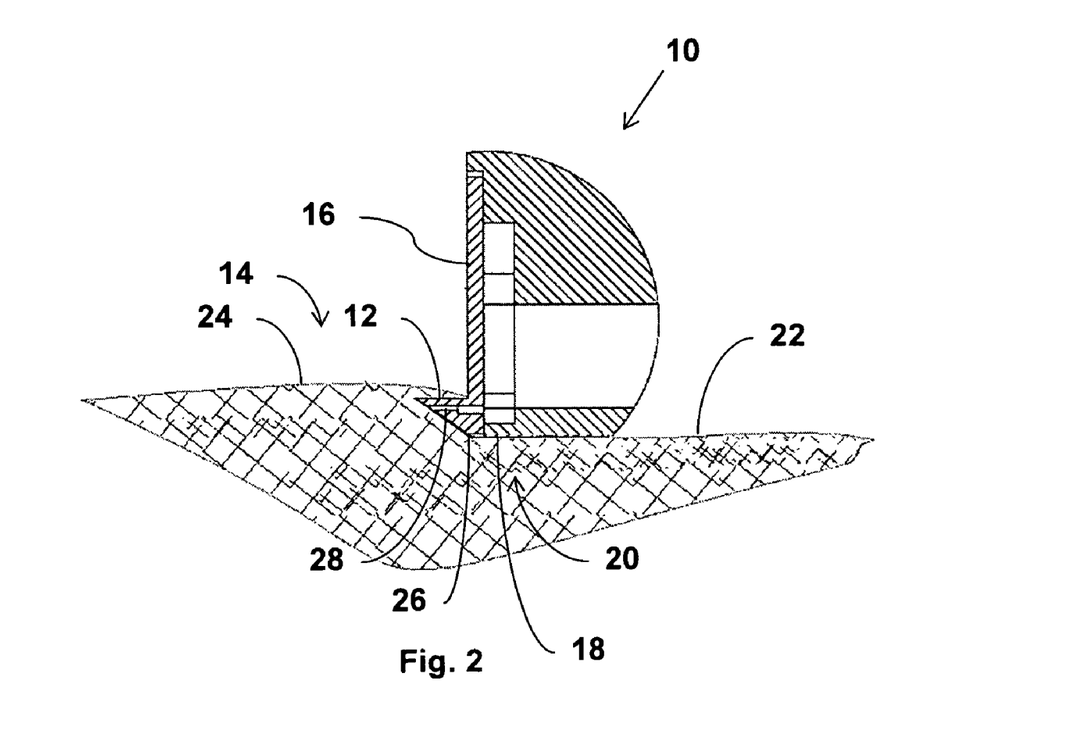

Referring now to the drawings, FIGS. 1 and 2 exemplify schematically a group of structures and corresponding methods according to the present invention. In general terms, these figures illustrate a delivery interface 10 employing a microneedle structure wherein a final position of one or more hollow microneedle 12 inserted into the biological barrier 14 is generally sideways projecting from the delivery configuration instead of the conventional downwards projecting arrangement. More particularly, the microneedle preferably projects from a relief surface 16 which is distinct from a primary biological-barrier contact region 18 of the delivery configuration, and typically angled upwards away from the biological barrier. This avoids the aforementioned problems of tissue pressure impeding fluid injection by ensuring that the fluid flow vector for injection is towards a non-compressed region of tissue. Furthermore, this configuration tends to provide an anchoring effect which locks the delivery configuration into the skin, thereby avoiding the aforementioned problems of leakage around the needles or ejection of the needles by back-pressure.

The method of the present invention relates primarily to the sequence of operations for insertion of the delivery configuration. Thus, contact region 18 is brought into contact with the biological barrier and moved in a motion having a component parallel to the surface of the flexible biological barrier so as to generate a boundary region 20 between a stretched portion 22 of the flexible biological barrier and a non-stretched portion 24 of the flexible biological barrier. Typically concurrently with at least part of this movement, and most preferably as a direct result of this movement, the at least one hollow microneedle 12 is caused to penetrate into the flexible biological barrier such that, at the end of the motion, hollow microneedle 12 extends into flexible biological barrier 14 from boundary region 20 in a direction towards non-stretched portion 24. A quantity of fluid is then injected through the bore of hollow microneedle 12 towards non-stretched portion 24.

At this stage, it will be appreciated that the present invention provides significant advantages over the conventional approach of microneedle insertion perpendicular to the skin surface. Specifically, the structure and corresponding insertion method of the present invention provide a microneedle fluid delivery interface with reliable sealed penetration of hollow microneedles in a manner which avoids the leakage and needle expulsion problems of the prior art. This and other advantages of the present invention will become clearer from the following detailed description.

Before addressing the features of various specific implementations of the present invention in more detail, it will be useful to define certain terminology as used herein in the description and claims. Firstly, the device is described as delivering a fluid into a flexible biological barrier. While the invention may be used to advantage for delivery of fluids through a wide range of biological barriers including the walls of various internal organs, the invention is primarily intended for delivery of fluids into layers of the skin of a living creature, and in particular, for intradermal or intraepidermal delivery of fluids into the skin of a human subject. The fluids delivered may be any fluids. Preferred examples include, but are not limited to, dermatological treatments, vaccines, and other fluids used for cosmetic, therapeutic or diagnostic purposes. Furthermore, although considered of particular importance for intradermal fluid delivery, it should be noted that the present invention may also be applied to advantage in the context of transdermal fluid delivery and/or fluid aspiration such as for diagnostic sampling.

Reference is also made to geometrical relations to the surface of the flexible biological barrier. For the purpose of the present description and the appended claims, all geometrical relations to the "surface" of the flexible biological barrier are defined in relation to a plane approximating to the surface of the barrier in an initial state of rest of the biological barrier, i.e., prior to any deformation of the barrier caused by insertion of the microneedle fluid delivery configuration. As a more technical definition, particularly important in the case of a region of skin which has considerable curvature, this surface is defined as the plane containing two orthogonal tangents to the flexible biological barrier surface at the location of interest.

Where reference is made to a direction of motion having a component parallel to the surface of the biological barrier, this includes any motion which is not perpendicular to the skin surface. Preferably, the motion has a majority component parallel to the skin surface, i.e., at an angle shallower than 45 degrees. Most preferably, the part of the motion performed in contact with the skin is performed substantially parallel to the skin's surface, i.e., with a motion vector not more than about ±15 degrees above or below the plane of the skin surface at rest.

With regard to angles relative to the plane of the skin, angles will be referred to relative to a vector parallel to the skin as zero degrees with angles pointing into the skin being positive and angles away (outwards) from the skin being designated negative. For simplicity of presentation, use may be made of the term "upwards" or "up" to refer to directions outwards from the initial plane of the skin and "downwards" or "down" to refer to directions inwards or towards the initial plane of the skin.

Reference is also made to various physical states of the biological barrier. The biological barrier is described as "stretched" when a distance between points defined on the barrier in at least one direction is greater than the distance between the same two points when the skin is released. The direction of maximum strain is referred to simply as the stretching direction. "Unstretched" denotes a state of the skin where no stretching is present parallel to the direction of stretching in an adjacent region of stretched skin. It will be appreciated that, where compression of skin tissue has lead to local bulging or folding of the tissue, a degree of stretching may occur perpendicular to the compression vector to accommodate the out-of-plane distortion of the tissue. Nevertheless, such tissue is referred to herein as "unstretched" since no elongation is present in the direction of stretching. Tissue for which the distance between points is reduced relative to the same two points when the skin is released is referred to as "relaxed" tissue since it exhibits lower surface tension than the skin when released.

Reference is also made to "depressed" or "raised" regions of the barrier. Depressed regions are defined as regions which lie below the initial plane of the skin, typically due to downward contact pressure applied thereto by a device, and raised regions are defined as regions lying above the initial plane of the skin, typically as the result of in-plane compression of an adjacent region of the skin.

The present invention is referred to as employing one or more microneedle. The term "microneedle" is used herein in the description and claims to refer to a structure projecting from an underlying surface to a height of no more than 1 mm, and preferably having a height in the range of 50 to 500 microns. The microneedles employed by the present invention are preferably hollow microneedles having a fluid flow channel formed therethrough for delivery of fluid. The height of the microneedles is defined as the elevation of the microneedle tip measured perpendicularly from the plane of the underlying surface. As mentioned above, most preferred implementations of the present invention employ microneedles of the type disclosed in co-assigned U.S. Pat. No. 6,533,949, namely, formed with at least one wall standing substantially perpendicular to the underlying surface and deployed so as to define an open shape as viewed from above, the open shape having an included area, and an inclined surface inclined so as to intersect with the at least one wall, the intersection of the inclined surface with the at least one wall defining at least one cutting edge. The fluid flow channel is preferably implemented as a bore intersecting with the inclined surface. The particular robustness of the aforementioned microneedle structure and its particular geometrical properties exhibit great synergy with the structures and insertion methods of the present invention, ensuring that the microneedles can withstand the applied shear forces and are optimally oriented for delivery of fluids into the biological barrier. These advantages with be detailed further below.

Reference is also made to various surfaces which may be provided by a "block of material". The term "block" is used herein to refer generically to any structure of one unitary element or plural elements cooperating to provide the recited surfaces in fixed mechanical relation. The "block" thus described includes, but is not limited to, a solid block, a hollow block, a thin sheet-like block and an open arrangement of surfaces mechanically interconnected to function together as a block. Part or all of the block may also be provided by a substrate upon which the microneedles are integrally formed.

The present invention is described with reference to a "fluid delivery interface" which relates to the structure and operation of the microneedle arrangement which interfaces with the biological barrier to create a fluid delivery path into the barrier. The fluid delivery interface may be integrated as part of a self-contained fluid delivery device, or as an adapter device for use with an external fluid supply device.

Finally with respect to terminology, the term "concurrently" is used herein in the description and claims to refer to two processes which occur in overlapping time periods. The term concurrently does not necessarily imply complete synchronicity and encompasses a range of cases including: synchronous occurrence of two processes, occurrence of one process during a time falling within the period of another process, and partially overlapping occurrence where a second process starts later, and continues later, than a first process.

Turning now again to FIGS. 1 and 2, it will be noted that the contact surface for moving in contact with the skin may be implemented in many different ways. Specifically, the contact surface may be a part 18 of a downward-facing surface of the delivery configuration, and/or may be provided by an edge region between surfaces 16 and 18. In the latter case, the edge may be a relatively sharp interface, or may be modified by a radius of curvature or any other desired modification, for example, texturing to increase frictional engagement with the skin surface. Optionally, at least part of the contact surface may be provided by a surface of hollow microneedle(s) 12 itself. By way of example, certain particularly preferred implementations of the method of the invention start by initially pressing the penetrating tips of the microneedles gently against the skin surface, thereby anchoring the tips in the skin. This further improves the efficiency of penetration and ensures positive engagement of the skin surface during the in-plane motion of the present invention. In this case, the microneedles themselves form part of the "contact surface".

As seen in FIG. 2, the stretched skin 22 and the non-stretched skin 24 are typically also distinguished from each other by a difference in level. The region of tissue under the device is generally depressed due to the applied contact pressure. The region of stretched skin lying behind the device also tends to be somewhat depressed relative to the initial level of the skin's surface. The non-stretched skin 24 is raised relative to the skin under the device, and is typically also slightly raised relative to the initial skin surface level. The raising of skin region 24 and/or the non-stretched or relaxed properties of the tissue are believed to contribute to a number of advantageous properties of the present invention. As mentioned earlier, the lack of downward pressure on the region into which the fluid is injected greatly reduces the back-pressure which impedes fluid injection. It is believed that the relaxation of the tissue due to in-plane compression and the resultant raising of the tissue also facilitates opening up of intradermal flow paths between dermal layers and thus facilitates accommodation of a larger quantity of injected fluid than would otherwise be possible and enhances dispersion within the dermal layers. It has also been observed that the fluid delivery interface as illustrated produces a locking effect which opposes withdrawal of the microneedles after insertion until the device is manually pulled out of the skin. Without in any way limiting the scope of the present invention other than as explicitly recited in the appended claims, it is believed that this locking effect may result from a downward force applied by the raised tissue 24 on microneedles 12 which in turn presses the contact surface 18 against the underlying tissue 20.

Microneedles 12 are described as extending from boundary region 20 towards non-stretched region 24. It should be noted that, depending upon the design of the contact surface(s) used, the penetration may occur either within or adjacent to the boundary region. The boundary region itself may vary from a significant area against which a surface of the device presses to a narrow line where a contact edge presses, or along which the microneedles themselves are anchored.

Figure 3:
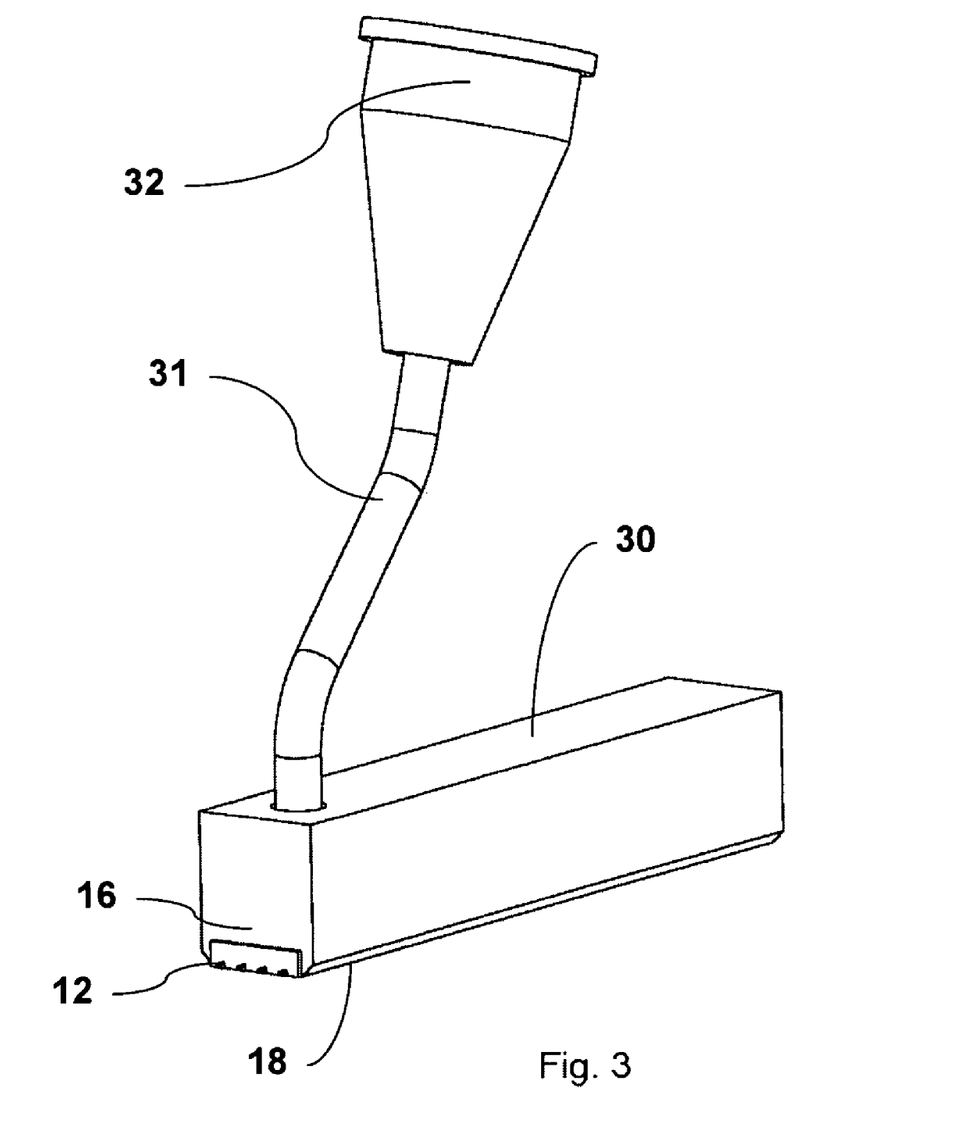
FIG. 3 is an isometric view of a fluid delivery adapter, constructed and operative according to the teachings of the present invention, the adapter including a row of microneedles in fluid connection with a flexible tube terminating in a luer connector.
Figures 4, 5, 6:
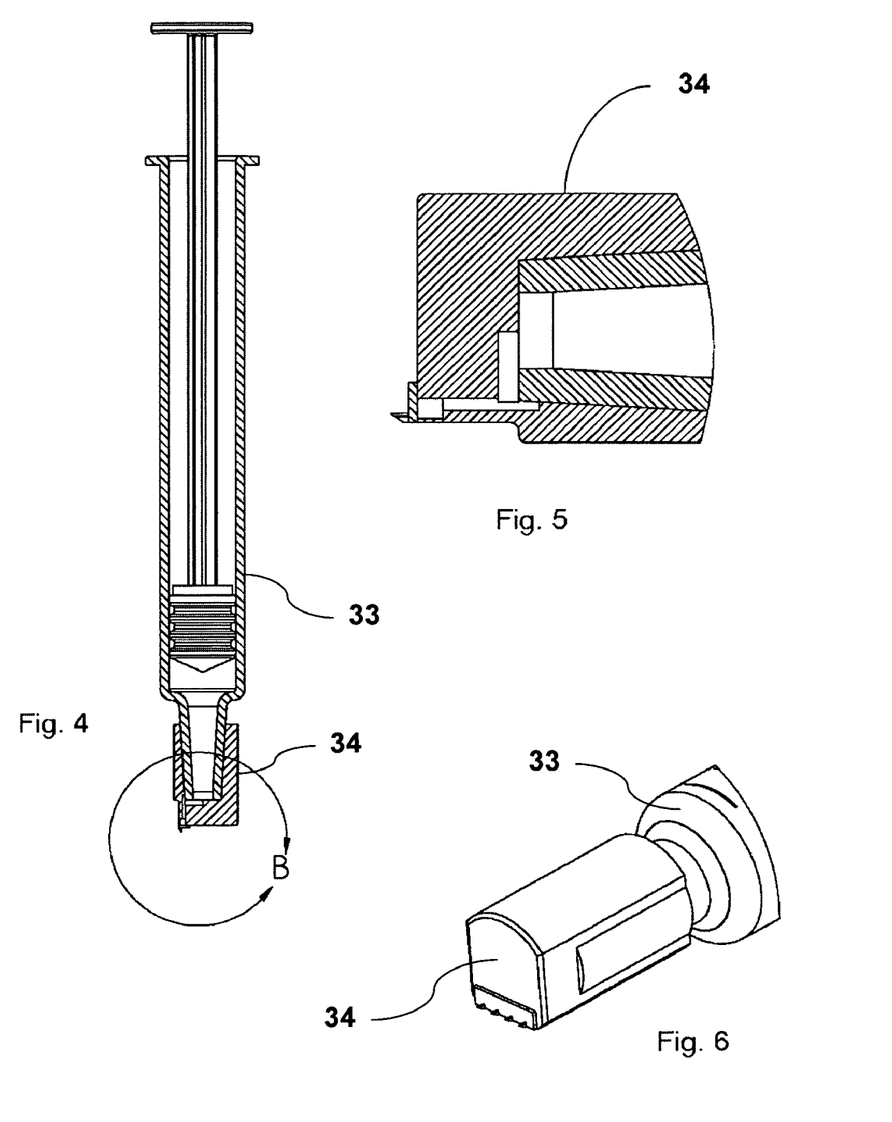
FIG. 4 is a cross-sectional view of a device, constructed and operative according to the teachings of the present invention, combining a pre-filled syringe with a microneedle fluid delivery configuration.
FIG. 5 is an enlarged view of the region of FIG. 4 labeled "B"
FIG. 6 is an enlarged isometric distal view of the microneedle fluid delivery configuration of the device of FIG. 4.

Although only one microneedle 12 is visible in the side cross-sectional views of FIGS. 1 and 2, it should be noted that most preferred implementations of the invention employ a linear array (row) of microneedles 12 extending substantially perpendicular to the direction of motion in contact with the biological barrier. Examples illustrating the use of a linear array of microneedles are shown in FIGS. 3 and 6. Optionally, separate microneedles may be in fluid connection with separate fluid supply flow paths/reservoirs for delivery of a plurality of distinct fluids at the same time or in a desired sequence. Alternatively, multiple microneedles may be connected to the same fluid supply, thereby achieving improved distribution of the fluid within the tissue and/or enhanced delivery rates. According to yet another option, fluid supply may be performed through only a subset of the microneedles with the other microneedles performing aspiration or being used only for anchoring the device more reliably within the tissue.

Hollow microneedle 12 is preferably mechanically associated with contact surface 18 such that the at least one hollow microneedle penetrates into the flexible biological barrier as a result of moving the contact surface. For maximum reliability and minimum manufacturing cost, certain preferred implementations of the fluid delivery interface of the present invention are formed with no moving parts wherein all required elements being in rigid mechanical relation. In this case, at least part of contact surface 18 is preferably provided by an edge 26 of a block 16, 18 of material, and microneedles 12 are preferably deployed on a face 16 of the block bordered by edge 26. As mentioned before, face 16 is preferably a "relief face", i.e., a surface which does not fully come in contact with the biological barrier when the device is first brought in contact with the barrier. To achieve this, face 16 is preferably angled up relative to the plane of face 18. The angle between faces 16 and 18, measured internally to the block, is preferably no more than about 150°, and more preferably no more than about 130°. In one particularly preferred implementation, edge 26 is formed between substantially orthogonal faces 16 and 18. Edge 26 is not necessarily, or even preferably, a sharp intersection of the planes of faces 16 and 18. For example, edge 26 may be rounded by a suitable radius of curvature.

While face 16 from which microneedles 12 project is preferably a release face as mentioned, it is important for the microneedles to be relatively close to the contact surfaces of the device so as to facilitate the microneedles coming into penetrating relation with the skin surface when deformation of the skin occurs. In quantitative terms, the distance from the plane of contact face 18 to the penetrating tip of microneedles 12 is preferably no greater than the height of the microneedles 12 measured perpendicular to face 16. In most preferred cases, the distance from edge 26 to the penetrating tip as measured parallel to face 16 is also less than the height of the microneedles. For the purpose of this description and the appended claims, the distance between two points measured parallel to a face or surface is defined as the distance between perpendicular projections of the points on to the face or surface in question.

Another preferred feature of the present invention relates to the flow vector for fluid delivery. Firstly, given that each hollow microneedle preferably has a bore 28 for delivery of fluid into the biological barrier, an extensional direction of the bore may be used to define the orientation of the microneedles. It is a preferred feature of the present invention that, at the end of the insertion motion, the bore extends into the biological barrier at an angle of no greater than 45 degrees to an initial plane of the surface of the flexible biological barrier. More preferably, the final position of the microneedles is such that the bore extends at an angle of no more than 30 degrees to the initial plane of the barrier, and in some cases, in a particularly preferred range of +15 degrees to the initial plane of the flexible biological barrier.

Another distinctive feature of both the systems and methods of the present invention is that the microneedles 12 of certain implementations of the present invention are preferably deployed in a "face down" orientation relative to the skin, in contrast to the "face up" orientation employed when using hypodermic needles. Thus, each microneedle is preferably formed with a "bevel surface", or with an inclined surface as described above in the context of the aforementioned co-assigned U.S. Pat. No. 6,533,949, which faces downwards. The intersection of the inclined surface with fluid flow bore 28 defines a fluid release aperture which is generally downward facing, i.e., towards the depth of the tissue. As a result of this orientation, the more upright microneedle wall surfaces face upward. This is believed to provide enhanced anchoring of the microneedle within the tissue, thereby facilitating the aforementioned lifting of the tissue ahead of the movement of the device. The downward opening fluid release aperture also ensures that any downward force exerted by the tissue on the microneedles does not tend to block off the fluid release aperture but rather, to the contrary, tends to open up the layers immediately beneath the microneedle tip and facilitate unimpeded fluid delivery or aspiration. Parenthetically, it should be noted that "face up" implementations also fall within the broad scope of the present invention and may, in certain cases, have advantages such as for particularly shallow injection.

With regard to the motion of insertion, the method of the present invention may be implemented with various different paths of motion for insertion of the microneedles as defined, so long as the contact surface(s) undergo a motion in contact with the skin which includes a component of motion parallel to the skin's surface. The motion may be a linear path, a pure rotation, or a more complex motion performed manually unaided, performed by use of a manually operated insertion guide arrangement, or fully automated by a robotic arrangement. The various motions are represented schematically by the combination of a straight arrow and rotation arrow in FIG. 1.

In each case where an edge 26 is employed as a contact surface, the edge is preferably substantially perpendicular to the component of the motion parallel to the surface. The face 16 from which the microneedles project is deployed ahead of edge 26 in the direction of motion. Where an array of microneedles is used, the linear array preferably extends substantially parallel to edge 26.

Having discussed many of the generic features of the present invention with reference to FIGS. 1 and 2, reference will now be made to a number of specific preferred implementations as illustrated in FIGS. 3-17D. Specifically, three devices for unguided manual insertion will be described with reference to FIG. 3, FIGS. 4-6 and FIGS. 14-17D, respectively, wherein the devices differ primarily in the implementation of the fluid delivery arrangements with which they are to be used. FIGS. 7-9 and FIGS. 10-13 illustrate two further implementations in which a guide arrangement defines the path of insertion motion of the fluid delivery interface.

Turning now to FIG. 3, this shows a simple implementation of a fluid delivery adapter including the fluid delivery interface of FIGS. 1 and 2 wherein the contact surface 18, relief surface 16 and microneedles 12 are implemented as part of an elongated block 30. Fluid flow paths (not visible) connecting all of the four microneedles are interconnected with a flexible fluid supply conduit 31 which has a connection port shown here as a luer connector 32. This facilitates use of standard fluid supply arrangements such as a syringe, an infusion set or a pressurized reservoir for providing the fluid to be delivered.

In use, block 30 is preferably first held at an angle of about 60° to the skin and gently pressed against the skin so that the tips of the microneedles become lodged in the skin. Although this preparatory step is generally not essential, it typically enhances operation of the device. The device is then lowered to a shallow angle relative to the skin, typically in the range of 10-30 degrees, and is urged forward across the skin so as to move with the skin through a path of typically between about 5 and about 15 millimeters. This motion achieves both the deformation of the skin and the microneedle penetration of the present invention concurrently. The device is then typically secured against the skin such as by applying surgical tape across the elongated body of block 30 and is ready for use by connection of the luer connector to a suitable source of fluid to be delivered, such as a syringe or an infusion set. It should be noted that the lateral deformation of the skin is employed for achieving penetration of the microneedles, but it is generally not necessary to maintain the sideways deformation during the fluid delivery process itself.

It will be noted that this embodiment of the device can be used with appropriate choice of microneedle dimensions, and possibly with minor adaptations, to provide flexible intradermal, intraepidermal or transdermal fluid delivery functionality similar to the ubiquitous heparin lock.

Turning now to FIGS. 4-6, these show an implementation of a fluid delivery device combining a syringe 33 with a microneedle fluid delivery interface 34 similar to that of FIGS. 1 and 2. In principle, syringe 33 may be a prefilled syringe permanently attached to interface 34 as part of a single-use disposable product. More preferably, microneedle fluid delivery interface 34 may be a modular replacement for a hypodermic needle configured for attachment to a range of standard syringes. In this case too, the fluid delivery interface 34 is preferably a single-use disposable item.

The mode of operation of the syringe implementation of FIGS. 4-6 is essentially similar to that of the implementation of FIG. 3 except that fluid delivery is typically performed immediately after insertion without securing the device to the skin, as is normal practice for syringe injections.

Figure 7:
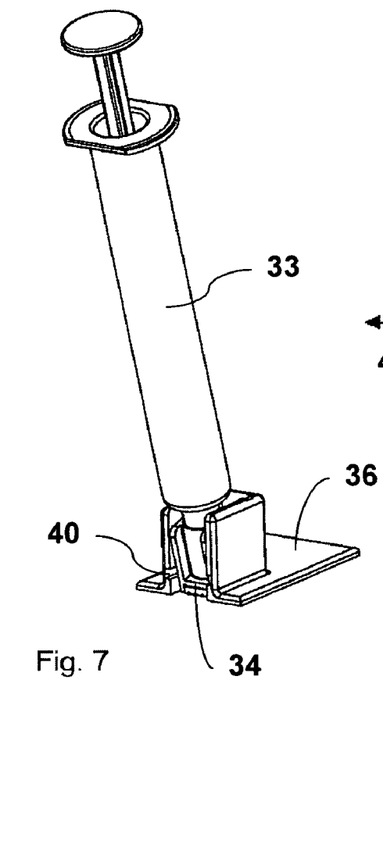
FIG. 7 is an isometric view of a variant of the device of FIG. 4, constructed and operative according to the teachings of the present invention, including a mechanical insertion guide arrangement for guiding movement of the microneedle fluid delivery configuration relative to the biological interface.
Figure 8:
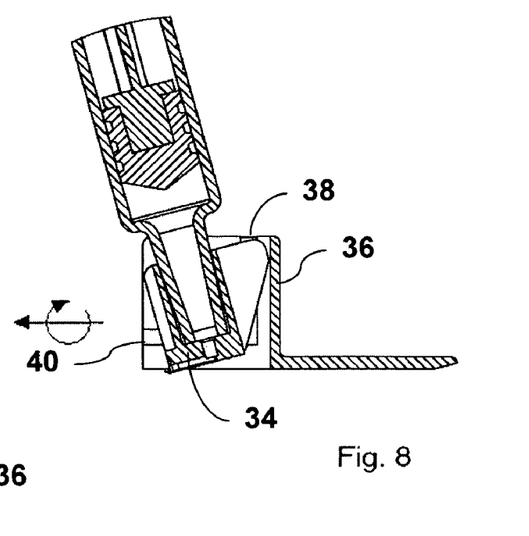
FIG. 8 is an enlarged partial cross-sectional view of the device of FIG. 7 prior to penetration.
Figure 9:
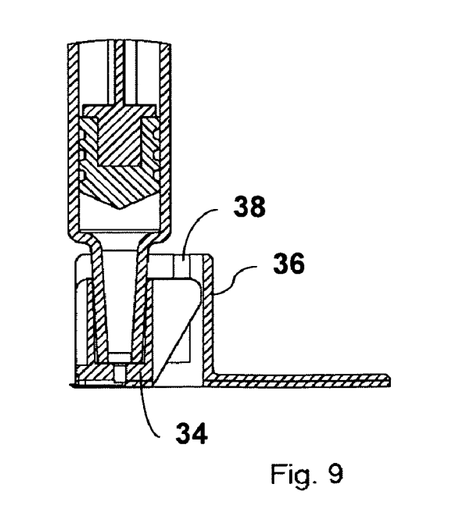
FIG. 9 is a view similar to FIG. 8 subsequent to penetration.

Turning now to the implementation of FIGS. 7-9, this is a variant of the device of FIG. 4 with addition of a mechanical insertion guide arrangement for guiding movement of the microneedle fluid delivery configuration relative to the biological interface. In this case, the fluid delivery interface 34 is configured to mate with a syringe which is deployed generally perpendicular to the skin surface. Interface 34 is deployed within a guide housing 36 which is either held or temporarily fixed to the skin surface such as by suitable medical adhesives and which cooperates with features of the interface and/or syringe to define a path of motion for insertion of the microneedle delivery interface. In the case illustrated here, interface 34 has a number of lateral projections (not shown) which engage a vertical guide slot 38 and a horizontal guide slot 40 formed on opposing side walls of the guide housing, thereby defining a path of relative motion between interface 34 and guide housing 36 from the starting position of FIG. 8 to the final position of FIG. 9. Although a simple pivotal engagement between interface 34 and guide housing 36 would provide a fairly similar path of motion, the use of vertical guide slot 38 is considered advantageous since it also provides a locking effect against unwanted withdrawal motion parallel to the skin's surface. When fluid delivery is complete, the syringe is tilted back towards the position of FIG. 8, thereby releasing the locking effect and allowing withdrawal of the microneedle assembly to the position of FIG. 8.

Figure 10:
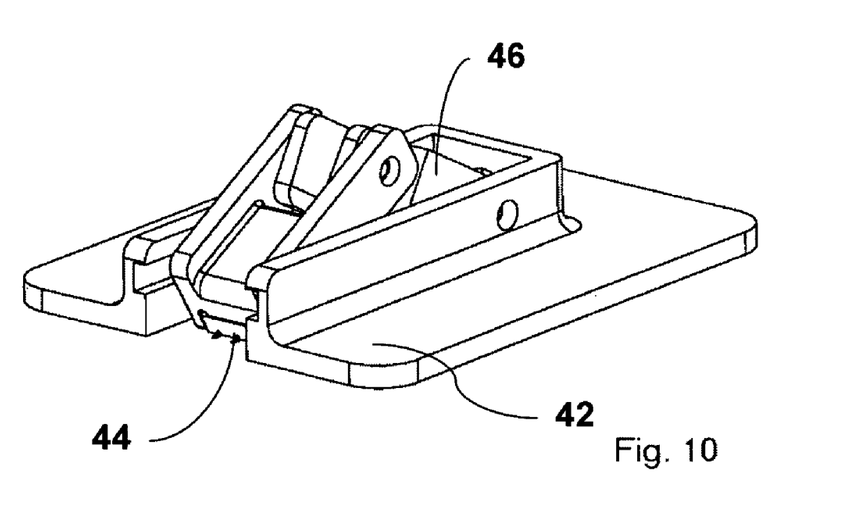
FIG. 10 is an isometric view of an alternative microneedle fluid delivery interface with a mechanical insertion guide arrangement, constructed and operative according to the teachings of the present invention, shown prior to penetration.
Figure 11:
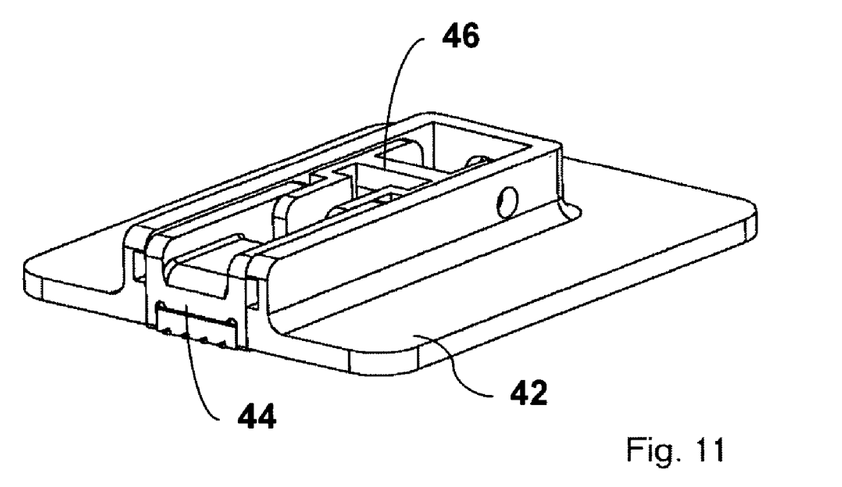
FIG. 11 is a view similar to FIG. 10 subsequent to penetration.
Figure 12:
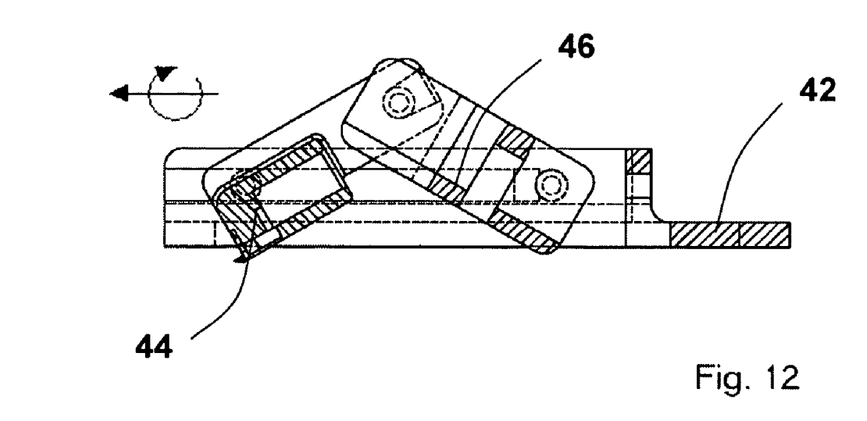
FIGS. 12 and 13 are cross-sectional views taken through the device as shown in FIGS. 10 and 11, respectively.
Figure 13:
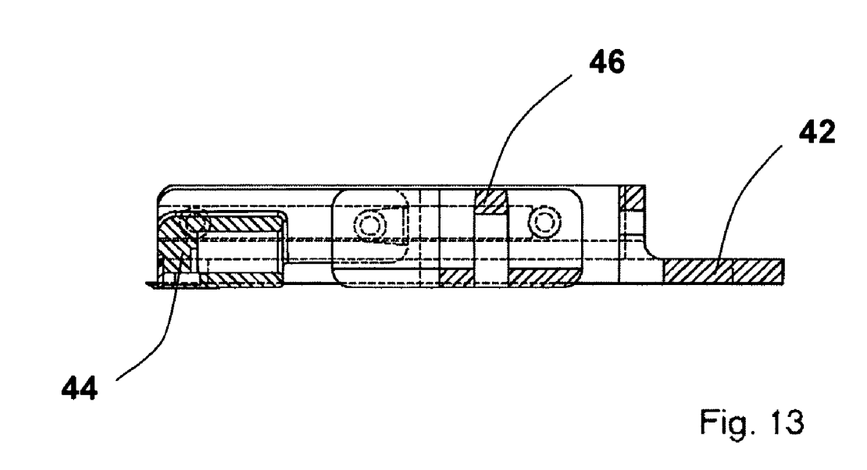
Figure 14:
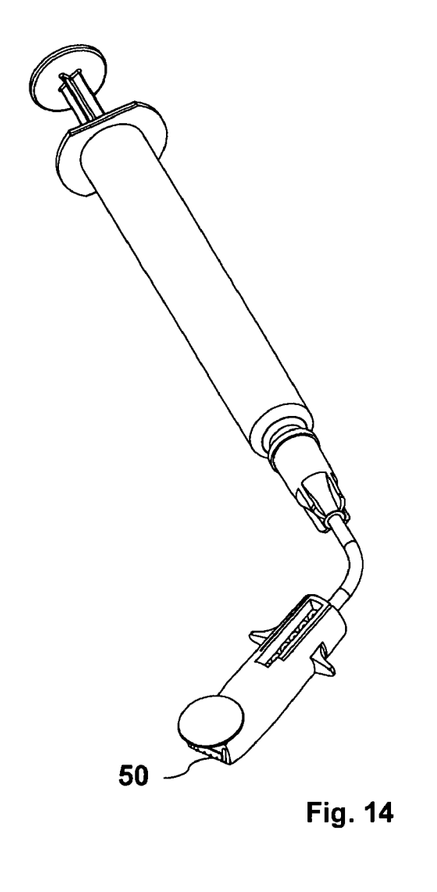
FIG. 14 is an isometric view of an alternative implementation of a microneedle fluid delivery device, constructed and operative according to the teachings of the present invention, shown together with an external syringe used for loading a fluid into the device.
Figure 15:
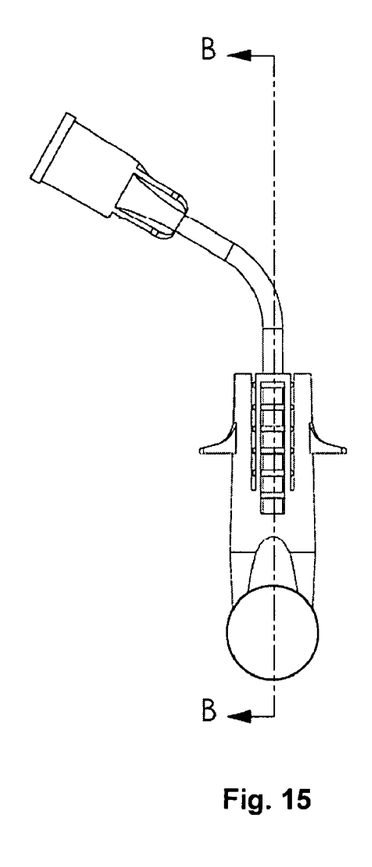
FIG. 15 is a top view of the device of FIG. 14 without the loading syringe.
Figure 16:
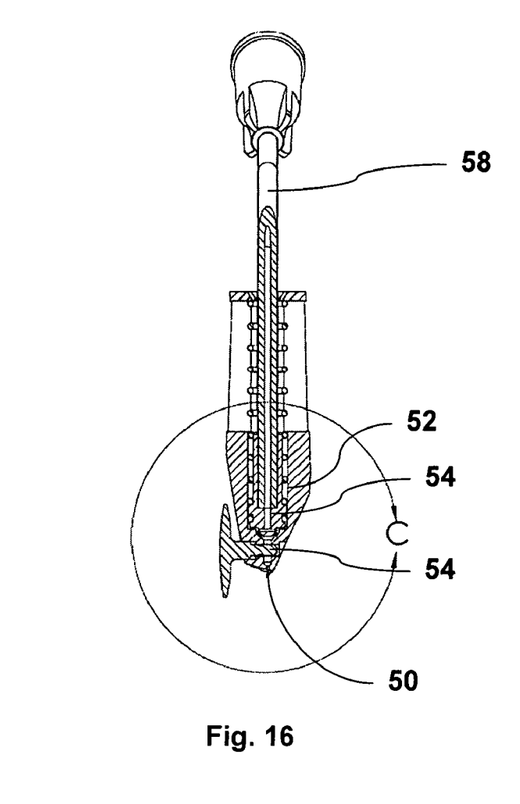
FIG. 16 is a cross-sectional view taken along the line B-B of FIG. 15.

Turning now to FIGS. 10-13, this shows a further alternative microneedle fluid delivery interface with a mechanical insertion guide arrangement. Here too, a guide housing 42 is either held against or temporarily fixed to the skin surface prior to movement of the microneedle fluid delivery interface from an initial position as shown in FIGS. 10 and 12 to a final position as shown in FIGS. 11 and 13. In this case, the delivery interface 44 is pivotally mounted on an arm 46 which is in turn pivotally mounted to housing 42. Lateral pins projecting from the delivery interface slide within corresponding slots in the housing to further define the path of motion. This structure also provides a mechanical locking effect in its deployed state of FIGS. 11 and 13. The device may adapted for any desired type of fluid supply (not shown) including attachment to a flexible tube and luer connector, direct connection to a syringe, or addition of a self-contained fluid supply reservoir, as will be clear to one ordinarily skilled in the art.

Turning finally to FIGS. 14-17D, this illustrates an alternative implementation of a microneedle fluid delivery device, constructed and operative according to the teachings of the present invention. In this case, the device has a self-contained fluid reservoir which provides a pressurized fluid supply for delivery via the microneedle fluid delivery interface.

Specifically, as best seen in FIGS. 17A-17D, the device includes a microneedle fluid delivery interface 50 generally similar to that of FIGS. 1 and 2 in fluid communication with a cylinder 52 within which a spring-biased piston 54 moves. A valve 56 is manually operable from a sealed position (FIGS. 17A and 17B) to an open position (FIGS. 17C and 17D) in which it allows fluid flow from the cylinder to the fluid delivery interface.

For loading a fluid into the device, an external syringe is preferably connected to a luer connector at the end of a flexible tube 58. The flexible tube feeds a conduit along the axis of the piston which leads to a one-way flow valve in piston 54. Fluid injected along the flexible tube therefore forces its way through the one-way valve in the piston so as to fill the side of the cylinder beyond the piston, thereby driving the piston to retract against bias of the spring from the position of FIG. 17A to the position of FIG. 17B. The external syringe is then removed and the device is ready for use. Optionally, the loaded device may be stored in this state for an extended period of time until required.

Figure 17A:
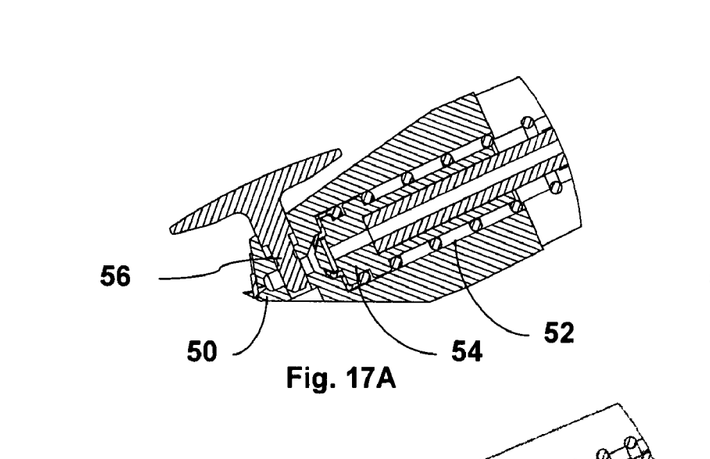
FIGS. 17A-17D are enlarged cross-sectional view of the region of FIG. 16 designated "C" showing the device prior to loading, subsequent to loading, immediately after triggering of delivery, and at the end of delivery, respectively.
Figure 17B:
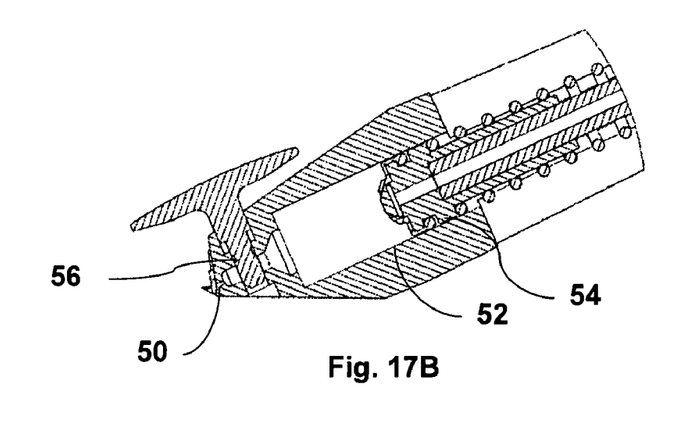
Figure 17C:
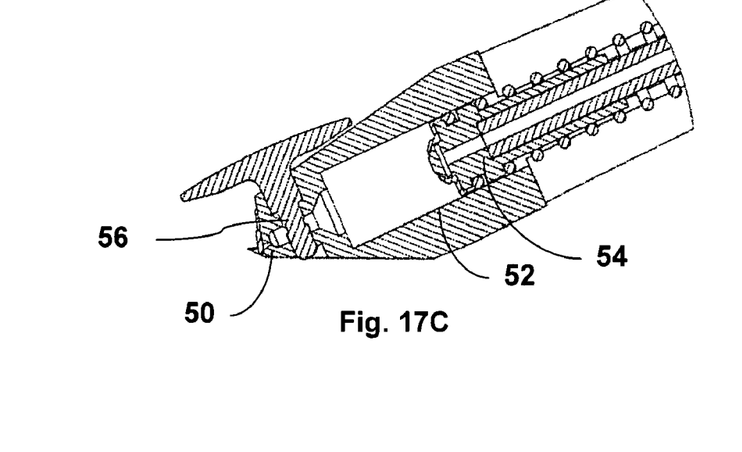
Figure 17D:
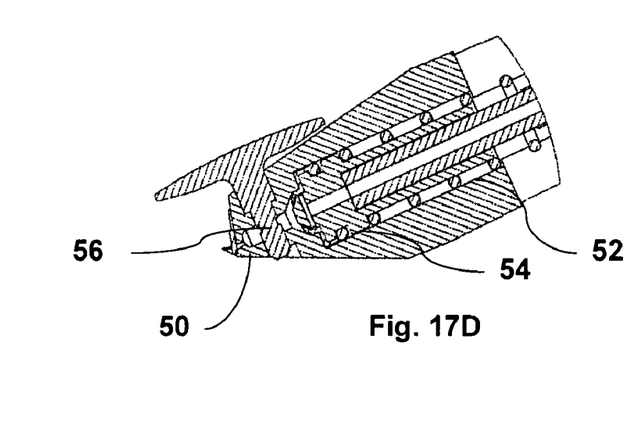

Application of the device to the skin of the user is essentially similar to that described above with reference to FIGS. 3 and 4-6. Alternatively, an insertion guide arrangement like that of FIGS. 7-9 or FIGS. 10-13 may be provided. Once the microneedle fluid delivery interface has been deployed in with the microneedles penetrating into the biological barrier, the actuator button of the valve is depressed (FIG. 17C) and the fluid starts to be delivered through the fluid delivery interface under a delivery pressure generated by the spring-biased piston. The fluid delivery then continues until the cylinder is empty, as seen in FIG. 17D. Preferably, the spring associated with piston 54 is preloaded to ensure effective delivery pressure right up until the end of the motion.

It will be appreciated that the above descriptions are intended only to serve as examples, and that many other embodiments are possible within the scope of the present invention as defined in the appended claims.

What is claimed is:

1. A device for delivering a fluid into a flexible biological barrier, the device comprising a fluid delivery interface including:
    (a) a first surface;
    (b) at least one microneedle projecting from said first surface and terminating at a penetrating tip;
    (c) a fluid flow bore extending through each microneedle; and
    (d) a contact surface deployed at an angle of no more than 150 degrees to said first surface as measured internally within said fluid delivery interface,
wherein said at least one microneedle is arranged with its penetrating tip adjacent to a plane of said contact surface such that, in use, when said contact surface is placed in contact with a biological barrier and moved with a component of motion parallel to said biological barrier towards said first surface, said at least one microneedle penetrates into a region of said biological barrier adjacent to, but not overlaid by, said fluid delivery interface.

2. The device of claim 1, wherein said first surface and said contact surface form between them an angle of no more than 130 degrees.

3. The device of claim 1, wherein said first surface and said contact surface are substantially orthogonal.

4. The device of claim 1, wherein said fluid flow bore of each microneedle extends at an angle of no greater than 45 degrees to said contact surface.

5. The device of claim 1, wherein said at least one microneedle has a height and terminates at said penetrating tip, a distance of said penetrating tip from the plane of said contact surface being no greater than said height.

6. The device of claim 1, wherein said at least one microneedle has downward-facing bevel surface, said fluid flow bore intersecting said downward-facing bevel surface to define a downward-facing fluid release aperture.

7. The device of claim 1, wherein said at least one microneedle includes:
    (a) one or more contiguous surfaces standing substantially perpendicular to said first surface, and
    (b) an inclined surface inclined so as to intersect with said one or more contiguous surfaces,
wherein said inclined surface is deployed on a side of said microneedle closest to said contact surface, and wherein said fluid flow channel intersects said inclined surface.

8. The device of claim 1, wherein said at least one microneedle has a height less than one millimeter.

9. The device of claim 1, wherein said at least one microneedle is implemented as a linear array of a plurality of microneedles.

10. The device of claim 1, further comprising a connector in fluid connection with said fluid flow bore and adapted for use with a fluid supply arrangement.

11. A device for delivering a fluid into a flexible biological barrier, the device comprising a fluid delivery interface including:
    (a) a first surface;
    (b) at least one microneedle mounted in fixed relation to said first surface so as to project from said first surface, said at least one microneedle terminating at a penetrating tip;
    (c) a fluid flow bore extending through each microneedle; and
    (d) a contact surface deployed in fixed spatial relation, and at an angle of no more than 150 degrees, to said first surface as measured internally within said fluid delivery interface,
wherein said at least one microneedle is arranged with its penetrating tip adjacent to a plane of said contact surface such that, in use, when said contact surface is placed in contact with a biological barrier and moved with a component of motion parallel to said biological barrier towards said first surface, said at least one microneedle penetrates into a region of said biological barrier adjacent to, but not overlaid by, said fluid delivery interface.

* * * * *